US009566419B2

(12) United States Patent
Frigstad et al.

(10) Patent No.: US 9,566,419 B2
(45) Date of Patent: Feb. 14, 2017

(54) BODY LUMEN OCCLUSION DEVICE AND METHOD

(75) Inventors: John R. Frigstad, St. Anthony, MN (US); James R. Mujwid, Crystal, MN (US); Karl A. Jagger, Deephaven, MN (US); William S. Tremulis, Redwood City, CA (US); Robert C. Grant, Minneapolis, MN (US)

(73) Assignee: Bayer HealthCare LLC, Whippany, NJ (US)

( * ) Notice: Subject to any disclaimer, the term of this patent is extended or adjusted under 35 U.S.C. 154(b) by 1043 days.

(21) Appl. No.: 12/756,762

(22) Filed: Apr. 8, 2010

(65) Prior Publication Data

US 2010/0262177 A1     Oct. 14, 2010

Related U.S. Application Data

(60) Provisional application No. 61/167,733, filed on Apr. 8, 2009.

(51) Int. Cl.
| | |
|---|---|
| *A61M 29/02* | (2006.01) |
| *A61B 17/12* | (2006.01) |
| *A61F 6/22* | (2006.01) |
| *A61B 17/00* | (2006.01) |

(52) U.S. Cl.
CPC .......... *A61M 29/02* (2013.01); *A61B 17/1214* (2013.01); *A61B 17/1219* (2013.01); *A61B 17/12022* (2013.01); *A61B 17/12109* (2013.01); *A61B 17/12159* (2013.01); *A61F 6/22* (2013.01); *A61F 6/225* (2013.01); *A61B 2017/00867* (2013.01); *A61B 2017/00898* (2013.01); *A61B 2017/12054* (2013.01)

(58) Field of Classification Search
USPC ........ 128/831, 832, 833, 887; 606/191, 192, 606/193, 197, 198
See application file for complete search history.

(56) References Cited

U.S. PATENT DOCUMENTS

| | | | |
|---|---|---|---|
| 6,193,728 B1* | 2/2001 | Ken et al. ...................... 606/108 |
| 6,705,323 B1* | 3/2004 | Nikolchev ....... A61B 17/12022 128/830 |
| 7,014,645 B2* | 3/2006 | Greene, Jr. ...... A61B 17/12022 606/158 |
| 8,157,855 B2* | 4/2012 | Eidenschink ............. A61F 2/91 623/1.15 |
| 8,235,047 B2* | 8/2012 | Swann et al. ................. 128/831 |
| 2005/0043755 A1* | 2/2005 | Wilson ............. A61B 17/12022 606/200 |
| 2007/0060946 A1* | 3/2007 | Keegan et al. ............... 606/200 |
| 2007/0227544 A1* | 10/2007 | Swann ............. A61B 17/12022 128/831 |

(Continued)

*Primary Examiner* — Ophelia A Hawthorne
(74) *Attorney, Agent, or Firm* — Jonathan Harris; Aseem Mehta (57) ABSTRACT

An occlusion device is described and depicted for occluding a body lumen. The device can comprise an occluding body member and one or more protruding portions or members disposed on the body member such that the protruding portion is provided with spacing, or surface area, to allow for tissue in-growth. The device can also comprise an expandable plug. The expandable plug may be twisted or otherwise formed into a shape, e.g., helical, in its initial deployment configuration, and untwist upon deployment.

14 Claims, 5 Drawing Sheets

(56) References Cited

U.S. PATENT DOCUMENTS

2009/0159088 A1* 6/2009 Karabey .......... A61B 17/12031
 128/831
2011/0259343 A1* 10/2011 Karabey .......... A61B 17/12031
 128/831

* cited by examiner

BODY LUMEN OCCLUSION DEVICE AND METHOD

RELATED APPLICATIONS

This application claims the benefit of U.S. Provisional Application No. 61/167,733, filed Apr. 8, 2009, the entirety of which is incorporated herein by reference.

BACKGROUND

Conventional contraceptive strategies generally fall within three categories: physical barriers, drugs and surgery. While each have certain advantages, they also suffer from various drawbacks. Barriers such as condoms and diaphragms are subject to failure due to breakage and displacement. Drug strategies, such as the pill and Norplant, which rely on artificially controlling hormone levels, suffer from known and unknown side-effects from prolonged use. Finally, surgical procedures, such as tubal ligation and vasectomy, involve the costs and attendant risks of surgery, and are frequently not reversible. Thus, there remains a need for a safe and effective method of contraception.

SUMMARY

In accordance with some embodiments of the present invention, an occlusion device for occluding a body lumen is disclosed, the occlusion device comprising an inner shaft or body member, and a plurality of fibers, sheets, molded features, or like protrusions on the inner member. In an embodiment, the occlusion device is insertable into the body lumen such that actuation or retraction of the inner member causes the stretched or otherwise longitudinally oriented protrusions to extend, group or bunch up together. The congregate structure created by the bunching protrusions provides the luminal occlusion. In turn, the contact of these bunching protrusions may create desired tissue trauma or denudation to further facilitate tissue in-growth. The aforementioned protrusions can include fibers, sheets, molded features along the inner member, spaced or linked plates, sponge or foam materials, or a myriad of other shaped or extended materials, such as polymers, Nitinol, and the like.

In one embodiment, the occlusion device includes a plug. The plug can be positioned within a coil or protrusion formation of the device. Upon deployment, the coil expands to a larger configuration or diameter within the lumen such that the plug can swell or expand to occupy the space within the coil. As such, the plug pushes against the lumen and further facilitates occlusion.

In one embodiment, the occlusion device can include a plug which is twisted or otherwise formed into a shape, e.g., helical, in its initial deployment configuration, and which untwists upon deployment. Denuding features may be attached or provided on the plug which can rotationally denude the body lumen to further facilitate tissue-ingrowth and occlusion.

The occlusion device in accordance with embodiments of the invention may be advanced to the desired location within the body lumen by a suitable delivery system, such as a delivery catheter or a conventional balloon catheter similar to those used for delivering stents, aortic grafts and various types of prosthesis. The device may be introduced and positioned within the region of the body lumen to be occluded with the device in the first configuration with a relatively small transverse or cross-sectional dimension. Once in place, the device, or the protruding portion in particular, may then be expanded to the second configuration with transverse or cross-sectional dimensions roughly corresponding to or slightly larger than the body lumen, so that the device can be secured to the wall defining the body lumen. The device may be self expanding or expanded by mechanical means. The device will then remain in the open configuration implanted in the body lumen.

With the open or expanded configuration, tissue in-growth, or epithelialization, through or into the framework or structure of the device, or its corresponding protruding portion, secures it to the wall defining the body lumen. At the same time, epithelialization through the device occludes the body lumen. Sufficient epithelialization to secure the device to the body wall and occlude the body lumen may take one or more weeks. While the term "epithelialization" is used herein, it should be understood that, depending on the body lumen, tissues such as endothelium or myocardium may be impregnating the device. Additionally, scar tissue formation may take place as well.

The occlusion device in accordance with embodiments of the invention may be used to provide effective sterilization or contraception for both males and females due to the tissue impregnated structure which occludes the reproductive body lumen and which has excellent durability. The device remains in place within the reproductive body lumen, and the tissue impregnated structure resists degradation or tearing, to thereby decrease the risk of failure of the device. Moreover, the implantation of the device can be performed in a single office visit, using minimally invasive and easily used devices such as hysteroscopes, catheters, guidewires, guiding catheters and the like. These and other advantages of the invention will become more apparent from the following detailed description of the invention when taken in conjunction with the accompanying exemplary drawings.

DETAILED DESCRIPTION

FIGS. 1A-3B illustrate an occlusion device comprising at least one inner shaft or body member 11 and one or more protrudable portions or members 14 extendable along at least a portion of the inner member 11. Occluding device may be a contraceptive or sterilization device for occluding a reproductive body lumen.

Figure 1A:
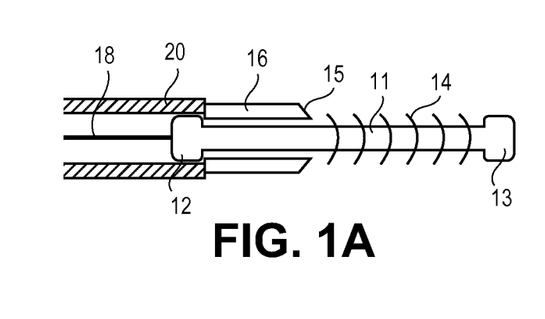
FIG. 1A is a schematic view of an occlusion device with protrudable/expandable members shown in a body lumen insertion configuration, in accordance with an embodiment of the present invention.
Figure 1B:
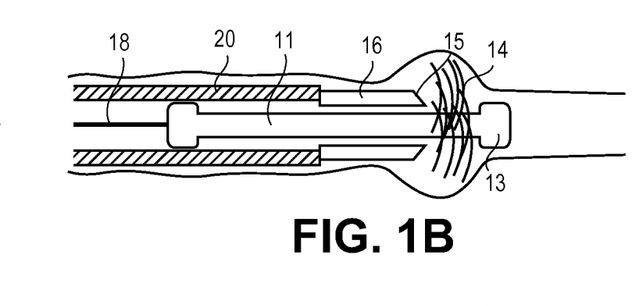
FIG. 1B is a schematic view of an occlusion device with protrudable/expandable members shown in a body lumen bunching/occlusion configuration, in accordance with an embodiment of the present invention.
Figure 1C:
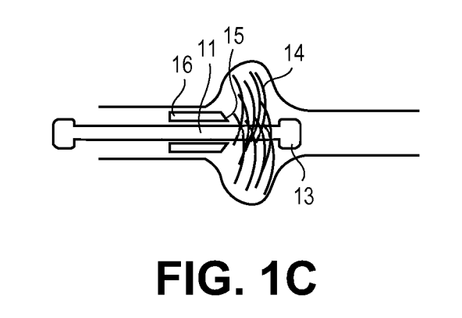
FIGS. 1C-1E are schematic views of an occlusion device deposited in a body lumen, in accordance with embodiments of the present invention.
Figure 1D:
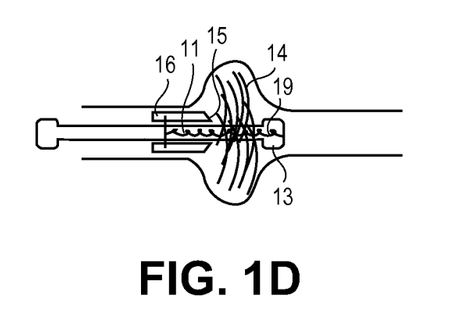
Figure 2A:
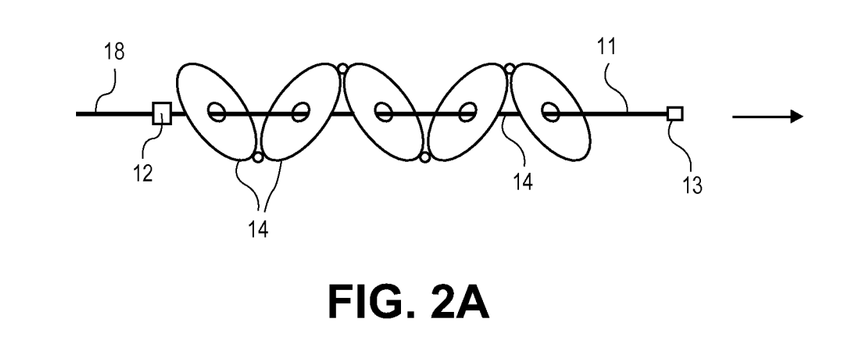
FIG. 2A is a schematic view of an occlusion device with protrudable/expandable plate members shown in a body lumen insertion configuration, in accordance with an embodiment of the present invention.
Figure 2B:
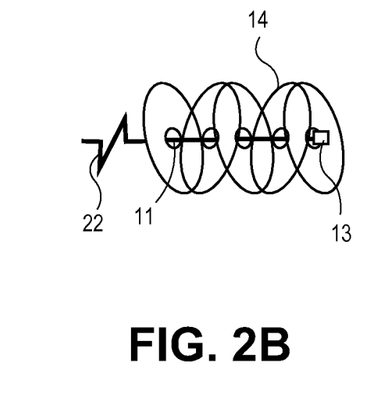
FIG. 2B is a schematic view of an occlusion device with protrudable/expandable plate members shown in a body lumen bunching/occlusion configuration, in accordance with an embodiment of the present invention.
Figure 3A:
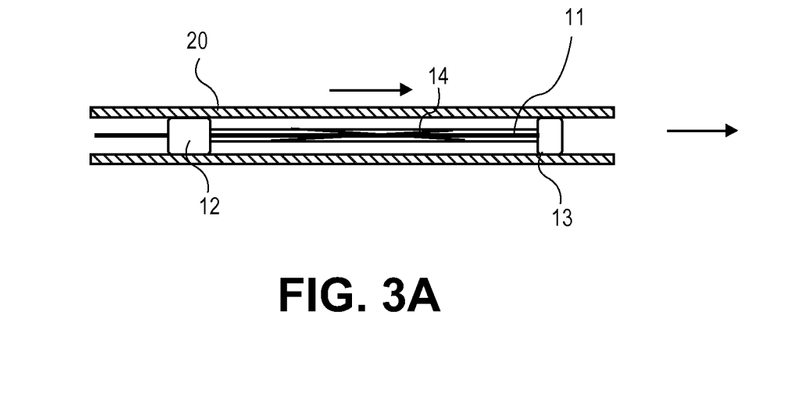
FIG. 3A is a schematic view of an occlusion device with protrudable/expandable members shown in a body lumen insertion configuration, in accordance with an embodiment of the present invention.

FIGS. 1A, 2A and 3A illustrate the occlusion device in a relatively small dimensioned configuration for introduction and advancement into the patient's body lumen. FIGS. 1B-1D, 2B and 3B illustrate the device in an open, expanded and relatively larger dimensional occlusion configuration. The device may have an open or spaced structure facilitating epithelialization which secures the device to the wall defining the body lumen. The device can be deformed to an expanded dimension, preferably equal to or slightly larger than the dimensions of the body lumen within which the contraceptive device is to be disposed. For disposition within a female patient's fallopian tubes the expanded transverse dimensions should be about 0.1 mm to about 5 mm.

In one embodiment, an outer sleeve 16 is disposed about an inner member 11, as shown in FIGS. 1A-1D. In an embodiment, outer sleeve 16 is slideable about inner member 11 (e.g. a shaft). For example, the outer sleeve 16 can include smooth, tubular inner surface which is slideable along an outer surface of inner member 11 between enlarged heads 12, 13. Alternatively, the outer sleeve 16 and inner member 11 can have matching threaded surfaces to guide movement of the outer sleeve 16 along inner member 11. One or more protruding members 14 (protrusions) are disposed along a length of the inner member 11. As illustrated in FIG. 1B, in an embodiment, once the device is inserted within the target body lumen, the outer sleeve 16 is held securely in place and the inner member 11 is retracted. In an embodiment, a cutting edge on the distal end 15 of the outer sleeve 16 strips the protruding members 14 off of the inner member 11 and/or slides the protruding members 14 along the inner member 11 such that the protrusions 14 are bunched together against an enlarged head 13 of the inner member 11, thereby increasing their respective cross-sectional dimensions within the lumen. These bunched protrusions 14 form the occlusion within the lumen, and may also form an immediate occlusion. To facilitate the expansion of the protrusions 14 through bunching, the protrusions 14 can be configured as fibers, sheets, molded features, and the like. Protrusions 14 may be independently coupled to the inner member 11, or bound together on inner member 11 to assist in bunching. In an embodiment, the protrusions 14 are woven around inner member 11. In an embodiment, the protrusions 14 are cast within an elastomer (e.g. silicone).

In accordance with some embodiments, in order to bunch the protruding members 14 together, the outer sleeve 16 and inner member 11 are moved relative to one another. In an embodiment, the outer sleeve 16 can abut against a sheath 20 of a delivery catheter in order to hold the outer sleeve 16 securely in place while the inner member 11 is retracted. In an embodiment, a retracting member 18 such as a guidewire can be utilized to actuate or retract the inner member 11. For example, the guidewire 18 may be retracted to slide a tubular inner surface of the outer sleeve 16 along an outer surface of the inner member, or the guidewire 18 may be rotated to retract the inner member 11 along the matching threaded surfaces. In an embodiment, retraction or rotation is continued until the outer sleeve 16 and inner member 11 are locked into place, for example by a contoured edge or thread. Once the protruding members 14 are bunched together, the device can be disconnected from the guidewire 18 and deployed within the body lumen, as illustrated in FIG. 1C.

In an embodiment, the occlusion device may be spring loaded such that the outer sleeve 16 is slideable about inner member 11. In such an embodiment, a spring 19 may connect the outer member 16 to the inner member 11 near the distal end 13. The occlusion device may be deployed within the body lumen by disconnecting the guidewire 18 from the occlusion device, thereby allowing the spring 19 to contract, causing the outer sheath 16 and inner member 11 to move relative to one another and bunch up the protruding members 14, as illustrated in FIG. 1D. The spring 19 may also function to keep the bunched protrusions 14 together between the outer sleeve 16 and the enlarged head 13.

Figure 1E:
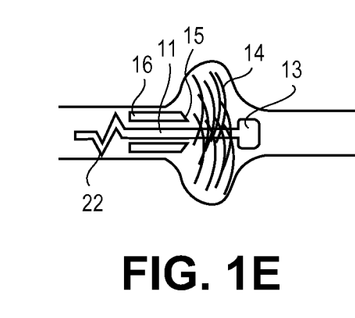

As illustrated in FIG. 1E, in an embodiment, a proximial portion of the occlusion device 11 or the guidewire 18 connected to the occlusion device may be cut and crimped 22 when deploying the occlusion device. The crimped portion 22 can be utilized to lock either of the outer sleeve 16 or bunched protrusions 14 into place from a proximal end of the deployed device. An enlarged head 13 can be utilized to lock the bunched protrusions into place from a distal end of the deployed device.

In an embodiment illustrated in FIGS. 2A-2B, the occlusion device can include an inner member 11, and a plurality of protrudable linked plates 14 running along a length of the inner member 11 between the enlarged heads 12, 13. The plates 14 are laid along the inner member 11 in a first configuration, for example a flat configuration, when the device is inserted into the body lumen, with the inner member 11 running through a center of each plate. While not illustrated, the device may be inserted into the body lumen by using any suitable means, such as a push rod to push the device out of a catheter, or withdrawing an outer sheath to expose the device. Following insertion, the inner member 11 is retracted, with the enlarged head 13 causing the plates 14 to bunch up against one another to increase the cross-sectional dimensions within the lumen. The occlusion device including bundled plates 14 can then be detached and left behind in the lumen to form the occlusion within the lumen. Similar to FIG. 1E, the occlusion device can be detached by cutting and crimping a portion 22 of inner member 11.

Figure 3B:
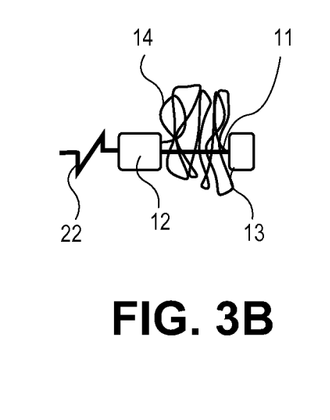
FIG. 3B is a schematic view of an occlusion device with protrudable/expandable members shown in a body lumen bunching/occlusion configuration, in accordance with an embodiment of the present invention.

In another embodiment, as shown in FIGS. 3A-3B, the occlusion device includes an inner member 11 and a plurality of protrudable members 14 pre-stretched along a length of the inner member 11 and connected at enlarged heads 12, 13. In an embodiment, the protrudable members 14 may be filaments constructed of PET, silicone, other polymer materials or films, metal fibers, nitinol, or like materials. As illustrated in FIG. 3A, an outer sheath 20 may retain the pre-stretched protrudable members 14 in the stretched configuration during insertion. The device may then be inserted into the body lumen by using any suitable means, such as a push rod to push the device out of a catheter, or withdrawing an outer sheath to expose the device. As illustrated in FIG. 3B, following insertion, the inner member 11 is retracted, allowing the pre-stretched protrudable members 14 to bunch up against the enlarged heads 12 and 13 and form the luminal occlusion. In an embodiment, as illustrated in FIG. 3B, the inner member is retractable through enlarged head 12. The occlusion device including bunched up members 14 can then be detached and left behind in the lumen to form the occlusion within the lumen. Similar to FIG. 1E, the occlusion device can be detached by cutting and crimping a portion 22 of inner member 11.

The bunched and deployed protrusion members 14 may provide a structure to promote tissue in-growth within the lumen. In an embodiment, the bunching of members 14 facilitates epithelialization, and the epithelialized structure occludes the reproductive body lumen sufficiently to prevent the passage of reproductive cells therethrough. In an embodiment, the bunched member 14 may provide immediate occlusion.

A variety of materials may be used to form the one or more of the protruding members 14 illustrated in FIGS. 1A-3B, including a superelastic or shape memory material such as a nickel-titanium (NiTi) alloy such as Nitinol, polymers, elastomers, thermoplastic elastomers, metals, fibers, films, and the like. Moreover, an irritant such as Dacron or Nylon, which promotes epithelialization, can be employed. Additionally, the one or more members 14 may be coated or otherwise impregnated with cell growth stimulators, hormones, and/or chemicals to enhance tissue impregnation.

The at least one inner member 11 illustrated in FIG. 1A-3B can be formed from metals such as stainless steel, Nitinol, platinum, tantalum, gold, or rigid or semirigid biocompatible plastics. Additionally, enhancing the surface area of the inner member 11 or members 14 can also provide greater adhesion for the epithelial tissue. Suitable surface treatments include plasma etching, sand blasting, machining and other treatments to roughen the surface. In other embodiments, the device may be coated or seeded to spur epithelialization. For example, the device can be coated with a polymer having impregnated therein a drug, enzyme or protein for inducing or promoting epithelial tissue growth.

In yet another refinement, at least part of the device, as for example the members 14, could be plated with or otherwise incorporate an inflammatory material to produce an inflammatory response in the tissue of the wall defining the body lumen, which further contributes to the obstruction of the lumen.

Figure 4A:
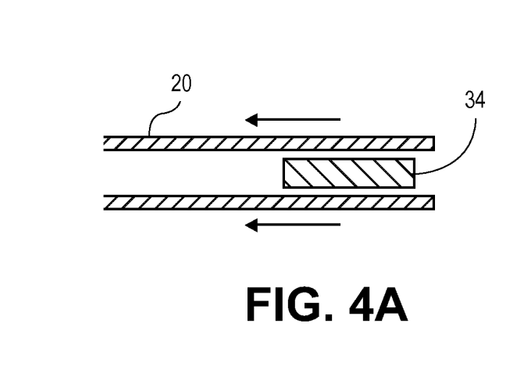
FIG. 4A is a schematic view of an occlusion device with a protrudable/expandable foam or sponge member shown in a body lumen insertion configuration, in accordance with an embodiment of the present invention.
Figure 4B:
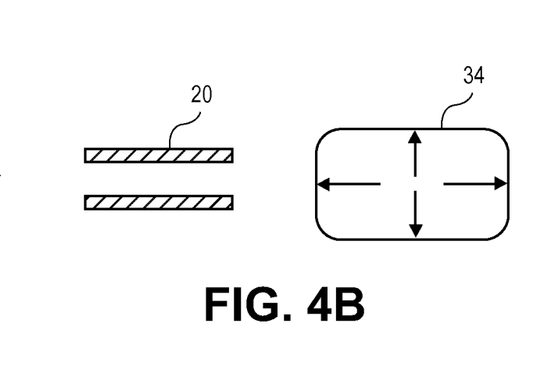
FIG. 4B is a schematic view of an occlusion device with a protrudable/expandable foam or sponge member shown in a body lumen expansion/occlusion configuration, in accordance with an embodiment of the present invention.

In another embodiment, the device can include a plug 34 with a first configuration of a relatively small dimension or diameter, as illustrated in FIG. 4A inside a delivery catheter sheath 20 prior to deployment. In an embodiment, the plug 34 can be formed of a sponge, foam or hydrophilic material. In an embodiment, a plug 34 is constructed of a closed cell structure on the interior and an opened cell structure on the exterior to allow for tissue in-growth. As illustrated in FIG. 4B, upon deployment, the plug 34 is adapted expand (e.g. by swelling) to a second configuration having a larger diameter or dimension. The expanded plug 34 can be left behind in the lumen to form the occlusion.

Figure 5A:
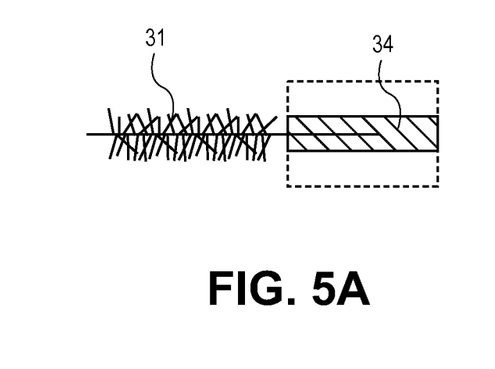
FIG. 5A is a schematic view of an occlusion device with a protrudable/expandable plug and additional protruding members, in accordance with an embodiment of the present invention.
Figure 5B:
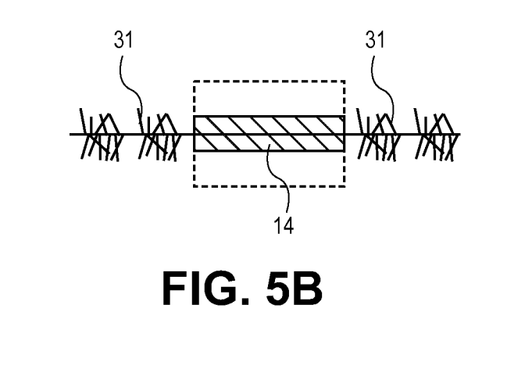
FIG. 5B is a schematic view of an occlusion device with a protrudable/expandable plug and additional protruding members, in accordance with an embodiment of the present invention.

In other embodiment illustrated in FIGS. 5A-5B, the occlusion device includes one or more inner members 31 attached or provided to extend out from the leading or trailing ends of the plug 34 to act as an additional tissue in-growth region or tissue anchoring means. For example, members 31 may include a plurality of fibers to promote tissue ingrowth, or other structural features such as barbs or hooks for anchoring.

Figure 6A:
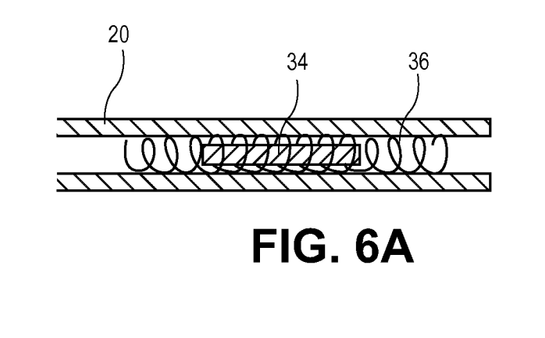
FIG. 6A is a schematic view of an occlusion device with a protrudable/expandable foam or sponge member and coil within a catheter in a body lumen insertion configuration, in accordance with an embodiment of the present invention.
Figure 6B:
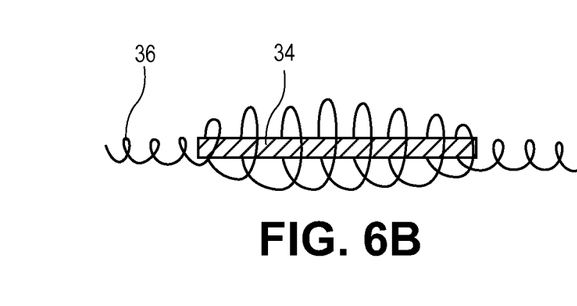
FIG. 6B is a schematic view of an occlusion device with a protrudable/expandable foam or sponge member and coil in an initial body lumen expansion/occlusion configuration, in accordance with an embodiment of the present invention.
Figure 6C:
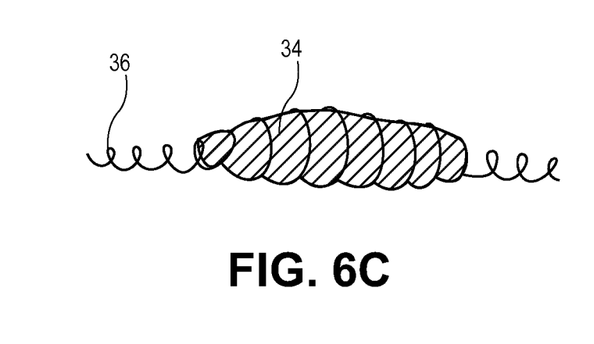
FIG. 6C is a schematic view of an occlusion device with a protrudable/expandable foam or sponge member and coil in a body lumen expansion/occlusion configuration, in accordance with an embodiment of the present invention.

In an embodiment, the occlusion device includes a preformed coil 36 and plug 34, as depicted in FIGS. 6A-6C. The coil 36 may further facilitate in denuding the lumen and promoting tissue in-growth. The plug 34 can be disposed within the coil 36 along a longitudinal axis of the coil 36. The coil 36 may be insertable within the body lumen via a catheter 20. The device may be deployed into the body lumen by using any suitable means, such as a push rod to push the device out of a catheter, or withdrawing an outer sheath to expose the device. As illustrated in FIG. 6B, upon deployment of the coil 36 from the catheter, the coil 36 will expand to a second larger configuration corresponding to its pre-formed dimensional limitations. The coil 36 may denude the inner surface of the lumen and over a relatively short period of time. As illustrated in FIG. 6B, the coil expands to have a larger expanded configuration or diameter in the middle portion, and a relatively smaller expanded configuration at the proximal and distal end portions. As such, the non-expanded plug 34 is retained within the expanded coil 36. As illustrated in FIG. 6C, the plug 34 then expands, for example by swelling, to accommodate the space within the expanded coil 36. This, in turn, causes the structure of the device to push up against the lumen to provide occlusion. In an embodiment, the outer surface of the plug 34 has an opened cell structure may contact the denuded lumen surface, thereby allowing for tissue in-growth.

Figure 7A:
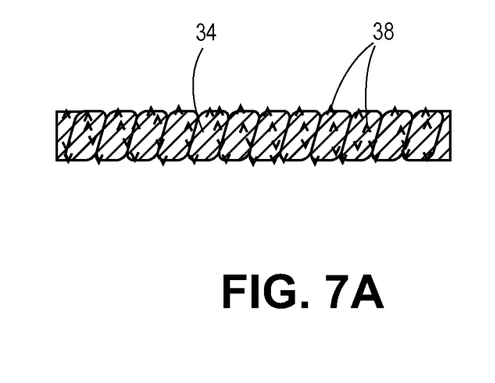
FIG. 7A is a schematic view of an occlusion device with a protrudable/expandable and twisted foam or sponge member, in accordance with an embodiment of the present invention.
Figure 7B:
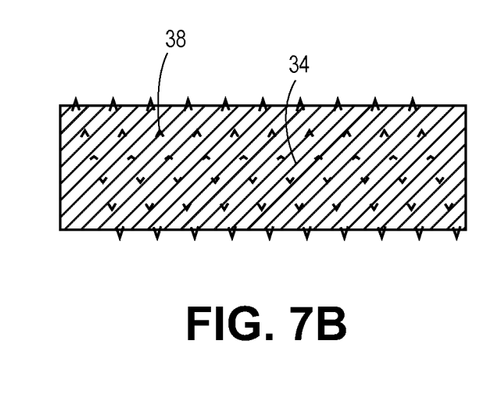
FIG. 7B is a schematic view of an occlusion device with a protrudable/expandable foam or sponge member having denuding features, in accordance with an embodiment of the present invention.

In an embodiment illustrated in FIG. 7A, the plug 34 can be twisted or otherwise formed into a shape, e.g., helical, in its initial deployment configuration. As the plug 34 is deployed, it unwinds. Additionally, one or more features 38 may be attached or provided along a portion of the plug 34, as shown in FIG. 7B. As such, when the plug 34 untwists and expands, the features 38 can rotationally denude the body lumen to further facilitate tissue in-growth and occlusion.

In still other embodiments, features 38 may include structural features such as barbs, edges and materials to assist in securing the expanded plug 34 to the vessel wall defining the body lumen. These barbs or other structural features become imbedded in the wall defining the body lumen as the plug 34 is expanded. Such anchoring features can be preferred for use in the fallopian tubes of a female patient, in order to prevent the peristaltic action therein from dislodging the device before epithelialization occurs.

In accordance with an embodiment illustrated in FIGS. 7A-7B, the plug 34 is twist-dry-loaded to a catheter for delivery. When dried in a twisted configuration, the plug has less pliability than when wet, and has increased stiffness which locks the twisted shape and stresses into the shape. When exposed to bodily fluids and hydrated in the body lumen, the plug 34 may swell and unwind to its native/low stress state based upon the internal stressed created during drying, and based upon which sections of the plug 34 are first exposed to and absorb bodily fluids.

While the occlusion device illustrated FIGS. 7A-7B is illustrated in isolation, it is understood that the occlusion device of FIGS. 7A-7B is also compatible with the occlusion devices illustrated in FIG. 4A-6C. A myriad of known plug 34 materials may be employed with embodiments of the present invention as illustrated in FIG. 4A-7B. For instance, hydrophilic materials, sponges or foams comprising water absorbing, pH-altered, ethyl vinyl acetate, polyurethane elastomer, silicone, and thermoplastic elastomer materials may be used. Moreover, the plug 34 may be doped with a drug or chemical, e.g., estrogen, to further promote tissue in-growth and wound healing.

Various modifications and improvements may be made to embodiments of the present invention without departing from the scope thereof. For example, while embodiments of the invention have been discussed primarily in terms of occluding a reproductive body lumen, the device may be used to occlude a variety of body lumens or passageways.

What is claimed is:

1. An occlusion system for occluding a body lumen comprising:
   a delivery catheter including:
      an outer sheath; and
      an occlusion device detachably coupled with the delivery catheter, the occlusion device including:
         an inner member having a proximal end, a distal end that forms a first enlarged head, and an outer surface;
         an outer sleeve that is slideable along the outer surface of the inner member between the proximal end of the inner member and the first enlarged head of the inner member; and
         a plurality of members movably and independently coupled to a portion of the inner member, wherein the plurality of members are spaced apart between the proximal end and the distal end when the device is in a body lumen insertion configuration; and
      wherein inserting the occlusion device within a target side of the body lumen causes the outer sleeve to slide along the outer surface of the inner member, thereby bunching up the plurality of members along a length of the inner member such that the plurality of members form a bunched protrusion with an expanded cross-sectional dimension when the device is in a body lumen occlusion configuration.

2. The occlusion system of claim 1, wherein the proximal end forms a second enlarged head and the outer sleeve is slideable along the out surface of the inner member between the second enlarged head and the first enlarged head.

3. The occlusion system of claim 2, wherein the outer sleeve further comprises a cutting edge on a distal end of the outer sleeve.

4. The occlusion system of claim 3, wherein the cutting edge strips the plurality of members off of the inner member.

5. The occlusion system of claim 1, wherein the occlusion device further comprises a spring that is attached to the outer sleeve and the distal end of the inner member, wherein the spring causes the outer sleeve and the inner member to move relative to one another and bunch up the plurality of members.

6. The occlusion system of claim 5, wherein the spring couples the outer sleeve with the inner member.

7. The occlusion system of claim 1, wherein the delivery catheter further comprises a retracting member detachably coupled with the occlusion device.

8. The occlusion system of claim 7, wherein the retracting member is coupled with the inner member.

9. The occlusion system of claim 1, wherein the occlusion device further comprises a retracting member that is configured to actuate or retract the inner member.

10. The occlusion system of claim 9, wherein the retracting member is rotated to retract the inner member along a matching threaded surface of the outer sleeve.

11. The occlusion system of claim 1, wherein said plurality of members are fibers.

12. The occlusion system of claim 1, wherein said plurality of members are sheets.

13. The occlusion system of claim 1, wherein the outer sleeve abuts against the outer sheath thereby holding the outer sleeve in place while the inner member is retracted.

14. The occlusion system of claim 1, wherein the outer sleeve and the inner member each form threaded surfaces such that sliding the outer sleeve along the outer surface of the inner member causes the outer sleeve to twist.

* * * * *